United States Patent [19]
Don Michael

[11] Patent Number: 6,006,138
[45] Date of Patent: Dec. 21, 1999

[54] NON-INVASIVE CARDIAC PACING

[75] Inventor: T. Anthony Don Michael, 4109 Sill Pl., Bakersfield, Calif. 93306

[73] Assignee: T. Anthony Don Michael, Bakersfield, Calif.

[21] Appl. No.: 09/095,799

[22] Filed: Jun. 11, 1998

[51] Int. Cl.[6] .................................................. A61N 1/362

[52] U.S. Cl. ............................................. 607/124; 607/10

[58] Field of Search ........................................ 607/124, 10

[56] References Cited

U.S. PATENT DOCUMENTS

| | | | |
|---|---|---|---|
| 4,304,239 | 12/1981 | Perlin | 607/124 |
| 4,640,298 | 2/1987 | Pless et al. | 607/124 |
| 5,056,532 | 10/1991 | Hull et al. | 607/124 |

*Primary Examiner*—Scott M. Getzow
*Attorney, Agent, or Firm*—Pillsbury Madison & Sutro

[57] ABSTRACT

Device and method for effecting ventricular cardiac pacing by inserting electrodes which are supported by a carrier into the stomach of a patient via the patient's esophagus, and pressing the electrodes against the wall of the stomach by the action of a carrier displacing member.

15 Claims, 2 Drawing Sheets

NON-INVASIVE CARDIAC PACING

BACKGROUND OF THE INVENTION

The present invention relates to non-invasive cardiac pacing, and is particularly directed to a method and device for transmitting electrical stimulation pulses to a heart ventricle, and monitoring cardiac function, by insertion of electrodes via the patient's esophagus, thereby avoiding the need for any surgical intervention.

It is already known in the art that atrial cardiac pacing can be performed by a procedure known as transesophageal pacing, in which one or more electrodes are introduced into a patient's esophagus to bring the electrodes to a point in the esophagus which is directly adjacent to the left atrium of the heart. A device of this type is disclosed in U.S. Pat. No. 4,706,688.

When electrodes are brought to such a position and are pressed against the wall of the esophagus, cardiac stimulation pulses can be applied to the heart atrium. When a condition requiring atrial pacing is encountered, this technique can prove advantageous since it allows pacing to be initiated rather quickly without requiring surgical intervention and the trauma associated therewith.

However, while there are certain situations in which ventricular pacing is indicated, there are no existing devices or procedures which allow ventricular pacing to be achieved safely in a manner similar to the transesophageal pacing technique described above.

BRIEF SUMMARY OF THE INVENTION

It is a primary object of the present invention to make possible ventricular pacing by means of a device which can be inserted through a patient's esophagus in order to bring an electrode or electrodes into position to effect ventricular pacing.

Another object of the invention is to provide a device for this purpose which is constructed to be safely and comfortably introduced into the patient's esophagus via a naris.

A further object of the invention is to enable effective ventricular pacing to be achieved by the application of low current pulses.

The invention is based in part on the realization that electrodes can be suitably mounted to enable them to first safely pass through the esophagus into the stomach and to then be pressed against the stomach wall at a location proximate to the patient's ventricle.

Thus, the above and other objects are achieved, according to the present invention, by a device for effecting ventricular cardiac pacing, comprising: cardiac pacing electrodes; a carrier supporting the electrodes in a manner to permit the electrodes to be inserted into the stomach of a patient via the patient's esophagus; and carrier displacing means supporting the electrodes and operable for pressing the electrodes against the wall of the stomach at a location adjacent a heart ventricle.

Objects according to the invention are further achieved by a method for effecting ventricular cardiac pacing comprising: inserting electrodes into a patient's stomach via the patient's esophagus; pressing the electrodes against a portion of the wall of the stomach which is adjacent a heart ventricle; and delivering electrical impulses to the electrodes for transfer to the heart ventricle as pacing pulses.

DETAILED DESCRIPTION OF THE INVENTION

Figure 1:
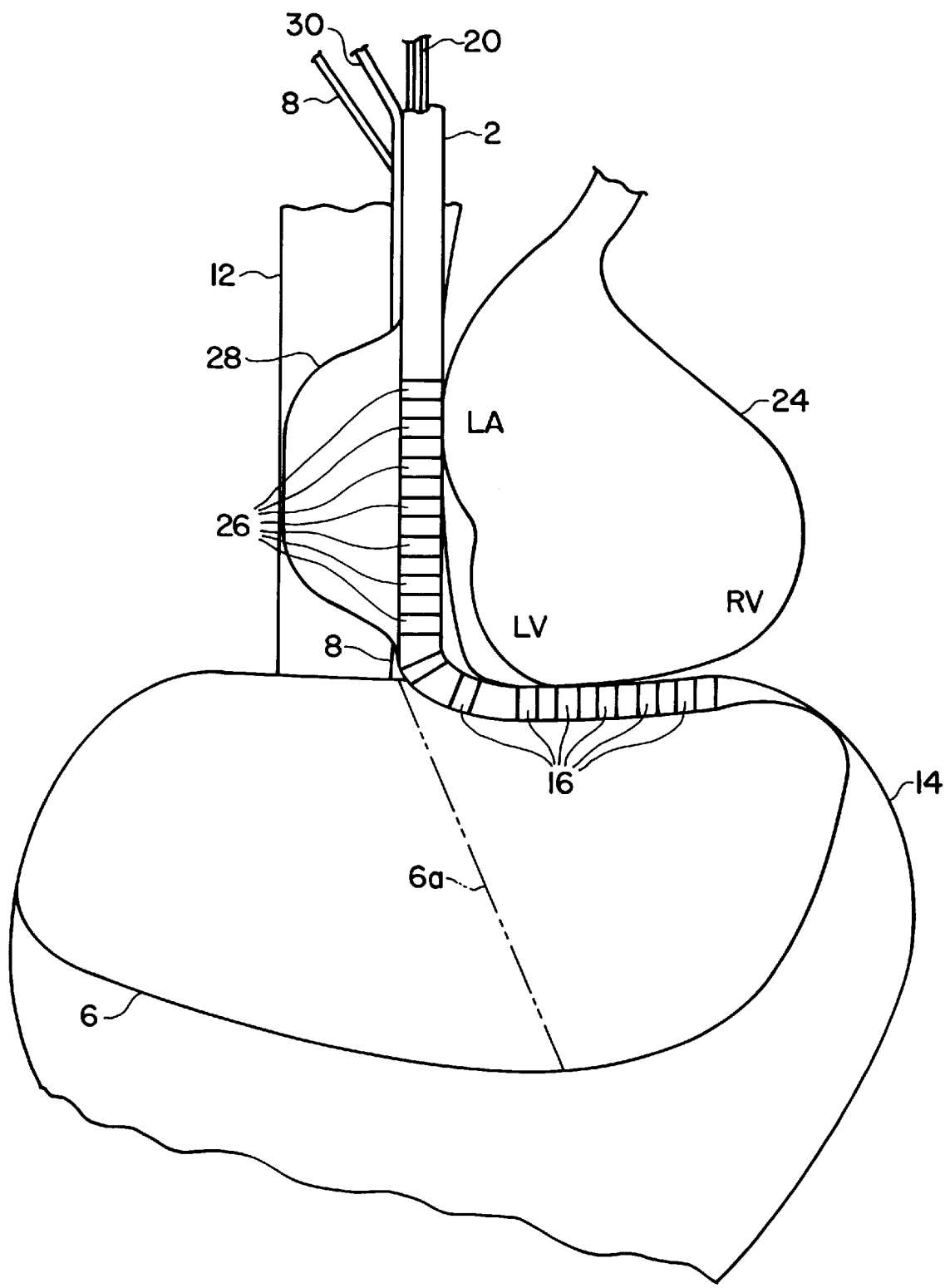
FIG. 1 is a pictorial, cross-sectional view showing the components of one embodiment of a device according to the invention in a position to effect ventricular pacing.

The device shown in FIG. 1 is composed basically of a tube, or catheter, 2 having a flexibility sufficient to enable it to be advanced through a patient's naris (not shown) and then through the patient's esophagus 12 so as to bring the leading, or distal, end of tube 2 into the patient's stomach 14. Balloon 6 is mounted on the distal end portion of tube 2. Balloon 6 may be inflated via an airway 8 that extends to the proximal end of tube 2, which would be located outside of the patient's body. The proximal end of airway 8 may be provided with an inflation bulb or other inflation device of the type commonly employed in medical equipment. In FIG. 1, balloon 6 is shown in its fully inflated state.

Tube 2 is provided, on its outer surface, with several annular electrodes 16, each connected to one respective conductor 20 that passes though tube 2 and extends to the proximal end of tube 2. The number, form and spacing of electrodes 16 will be selected on the basis of principles already known in the art.

The patient's heart 24 is normally located relative to esophagus 2 and stomach 14 in substantially the manner shown in FIG. 1, with its left ventricle in close proximity to, or in contact with, the wall of stomach 14, its right ventricle in proximity to the wall of stomach 14 and its left atrium in close proximity to, or in contact with, esophagus 12.

According to the invention, two or more electrodes 16 are pressed, as a result of inflation of balloon 6, against the inner surface of the portion of the wall of stomach 14 which is in proximity to, or in contact with, at least the left ventricle of heart 24, and possibly also against the inner surface of the portion of the wall of stomach 14 which is in proximity with the right ventricle of heart 24. Balloon 6 may be given a compliance and may be dimensioned so that balloon 6 will, upon being inflated, act to slightly distend the associated the portion of the wall of stomach 14 to an extend sufficient to place that stomach wall portion in contact with the outer surfaces of one or both ventricle chambers. Then, electrical impulses conducted to electrodes 16 via conductors 20 will be conducted to heart 24 through the stomach wall to act as ventricular pacing pulses.

Due to the fact that balloon 6 can press electrodes 16 firmly against the stomach wall, and can press the stomach wall against at least one ventricle, electrodes 16 can be given small dimensions and low level pacing currents can be used.

Tube 2 of a device according to the present invention could be constructed on the basis of principles well known in the art and can be constituted by any tubular body having the requisite flexibility. This tube could be constituted, for example, by a device known as a tapscope, examples of which are marketed by the Arzco Corporation. Tube 2 could also be identical to a known tube used for transesophageal pacing, as disclosed in the above-cited U.S. Pat. No. 4,706,688. Tube 2 may also be a flexible catheter made of electrically insulating material.

Balloon 6 can be secured to a distal end portion of tube 2 in any suitable manner already known in the art for securing balloons to catheters and other medical devices. When balloon 6 is not inflated, it will not offer any impediment to insertion of the device through a naris and then through the esophagus. In addition, When balloon 6 is not inflated, tube 2 will assume its normal generally straight configuration, thus allowing it to pass easily and safely through the esophagus, while having sufficient flexibility to follow curves or bends in the esophagus. When tube 2 has been inserted to a final position, where a portion of its distal end projects by an appropriate amount into stomach 24, balloon 6 can be inflated, using an inflation fluid such as air or water introduced via airway 8, to deflect the distal end portion of tube 6 into the configuration shown in FIG. 1, so that at least two electrodes 16 press against the inner wall of stomach 14.

Then, a pulling force may be applied to the distal end of tube 2 to help press the electrodes against the stomach wall. Prior to insertion of tube 2, the patient's nasal passages will be locally anesthetized. Experience with other medical procedures involving nasal insertion of a tube have shown that the requisite pulling force will not cause unacceptable patient discomfort. Thereafter, pacing pulse may be applied between a selected pair of electrodes, or heart activity may be monitored by connecting one or more electrode pairs, via associated conductors 20, to monitoring equipment located outside of the patient's body.

Balloon 6 may be made of any suitable, resiliently stretchable material of the type normally employed in medical devices, one suitable material being rubber latex. Balloon 6 can have homogeneous physical characteristics, including a homogeneous compliance, or balloon 6 can be made so as to have two subportions with respectively different compliances, compliance representing the ease with which a material can be stretched, and high compliance signifying greater ease of stretchability than does low compliance. This can be achieved by manufacturing the two subportions to have respectively different thicknesses or by fabricating the balloon in a manner such that the two subportions have respectively different compositions. In either event, balloon 6 can have a one-piece construction.

The change in characteristics between subportions can take place at an appropriate transition region whose location is represented generally by the line 6a in FIG. 1. In this case, the subportion to the right of line 6a would have a higher compliance than the subportion to the left thereof so that the subportion carrying tube 2 expands preferentially to press electrodes 16 against the inner surface of the wall of stomach 14.

The electrodes on tube 2 may be constructed and mounted in the same manner as the electrodes disclosed in the above-cited U.S. Pat. No. 4,706,688. Tube 2 can have a relatively small diameter, for example as small as 7 French, and can have a flexibility which enables it to be safely introduced to the patient's esophagus via a naris. This mode of introduction has been found to be less uncomfortable for the patient than oral introduction.

In further accordance with the invention, electrodes 16 can, as shown in FIG. 1, be supplemented by identical electrodes 26 disposed along a length of tube 2 at a location to act on an atrial region of heart 24, in the manner disclosed in U.S. Pat. No. 4,706,688, cited above. Each electrode 26 is also connected to a respective conductor 20 so that pacing pulses may be generated between an adjacent pair of electrodes or heart signals can be supplied to external monitoring equipment. Also as disclosed in U.S. Pat. No. 4,706,688, tube 2 carries a cuff, or balloon, 28 which is inflatable to press one or more pairs of electrodes 26 against esophagus 12 at a location adjacent an atrial portion of heart 24.

Electrodes 26 and cuff 28 have the same structure as disclosed in U.S. Pat. No. 4,706,688, as do all components, such as an airway member 30 for inflating cuff 28 and conductors 20 connected to electrodes 26. For this reason, the entirety of U.S. Pat. No. 4,706,688 is incorporated herein by reference.

Ventricular and/or atrial pacing pulses can be generated by applying electrical voltage pulses between an adjacent pair of electrodes 16 or 26, this representing bipolar pacing, or between any one of electrodes 16, 26 and an extended electrode secured to the patient's chest, this representing ambipolar pacing. Correspondingly, cardiac activity can be monitored by sensing electrical pulses created between an adjacent pair of electrodes or between any one electrode 16, 26 and the external electrode.

A plurality of spaced electrodes 16 are provided to allow for individual variations in the precise position of heart 24 in the body. If the exact location of each electrode is not known, the same stimulating pulses can be applied to adjacent electrode pairs in the case of bipolar pacing, or adjacent electrodes in the case of ambipolar pacing.

Thus, a device as disclosed herein can be selectively used to effect ventricular and/or atrial pacing and/or monitoring.

According to a further feature of the present invention, the novel device disclosed above can be utilized in a system for performing electrophysiological testing, possibly on an outpatient basis. Such a system is employed, for example, to custom test a pacemaker which is to be implanted in a patient and to pretest the heart prior to pacemaker implantation. Heretofore, this has been done by surgically implanting between five and seven electrodes at different points in the heart chambers, applying pacing pulses having different characteristics, and monitoring the heart response with electrocardiographic (EKG) device. Such a procedure is known as preprogramming.

Both the application of atrial and ventricular pacing pulses and monitoring of cardiac response can be performed in a system using a pacing device according to the invention, introduced into the patient's esophagus and stomach. Thus, one phase of surgical intervention can be eliminated.

Figure 2:
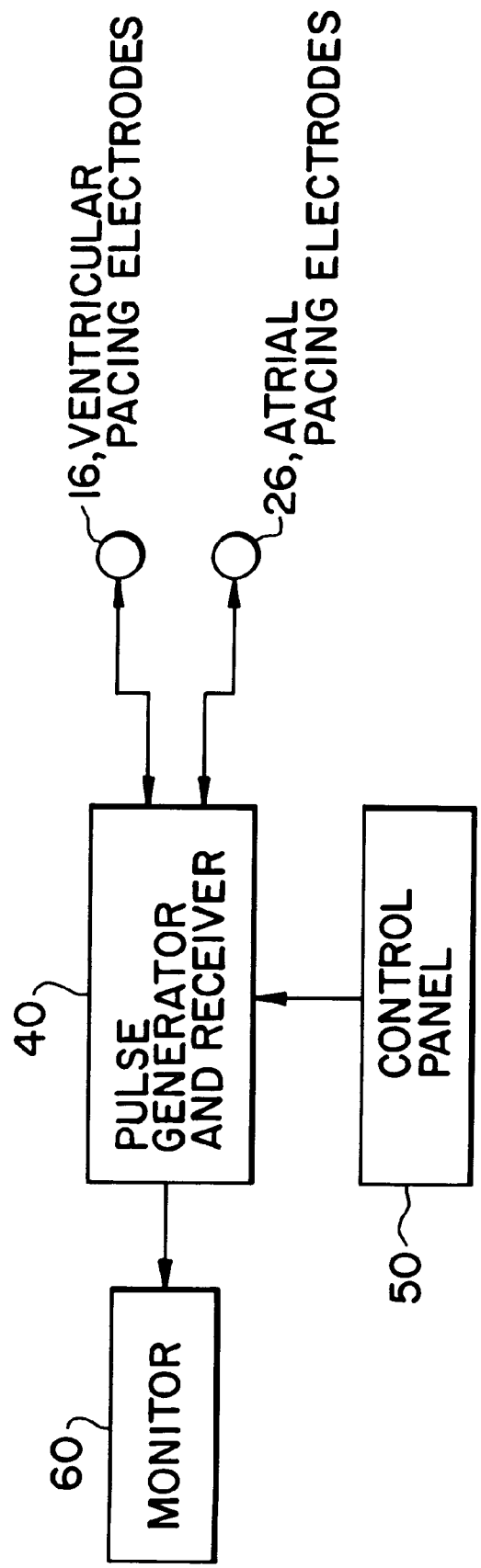
FIG. 2 is a block diagram of one embodiment of a testing system according to the present invention.

One embodiment of an electrophysiological pacing and monitoring system according to the invention is shown in FIG. 2. This system includes the device of FIG. 1, represented in FIG. 2 only by electrodes 16 and 26, a pulse generator and receiver 40, a control panel 50 and a monitor 60.

Pulse generator and receiver 40 is connected to supply pacing pulses to a selected pair of electrodes 16 and a selected pair of electrodes 26 and to receive electrical signals arising in the heart and applied to the selected electrodes 16 and/or 26. The timing, frequency, pulse duration and magnitude of the electrical pulses delivered to electrodes 16 will also be determined on the basis of principles, and particularly biopolar pacing principles, already well-known in the ventricular pacing art.

Control panel 50, which may be a keyboard, is connected to pulse generator and receiver 40 for inputting commands to control the timing, amplitude and duration of pacing pulses.

Monitor 60 is connected to pulse generator and receiver 40 to display parameters of pacing pulses being outputted and associated heart responses. Monitor 60 may be a CRT, LED, LCD, plotter, printer, etc., and may display any desired combination of signal waveforms and alphanumeric data representations.

Components 40, 50 and 60 may be constituted by known electrophysiological testing systems. With regard to pulse generator and receiver 40, systems for generating heart pacing pulses and for processing signals resulting from cardiac activities are already well known in the art and the assembly and operation of such systems for purposes contemplated by the present invention are well within the capability of those skilled in the relevant art or arts.

As an example of operations that can be performed with apparatus according to the invention, atrial pacing pulses can be applied to electrodes 26 at a preset rate for a selected time period. These pacing pulses are then halted and the sinus node recovery time is measured. This measured time provides an indication of the function of the sinus node.

According to another example, atrial pacing pulses can be applied to electrode 26, and the AV delay, which is an indication of the time required to conduct an atrial impulse to the ventricle, is measured. Atrial pacing can be used to overdrive and correct arrhythmias. The contribution of actual pacing to heart function can be assessed in comparison to the contribution of ventricular pacing alone.

According to another possibility, ventricular pacing pluses are applied to electrodes 16 and the VA time, or the time required to conduct such pulses from the ventricle to the atrium, is measured. In addition, extra impulses can be used to reduce and correct, and to test the effects of medication on, arrhythmias.

Such pacing pulses can also be employed to detect or correct arrhythmias. If arrhythmias are detected, these can either be converted by electrical shock, or paced out by increasing the rate of ventricular or atrial pacing pulses.

In addition, the system according to the present invention can be utilized to perform other functions that are now performed by implanted pacemakers, including monitoring of drug therapy and monitoring of implanted pacemaker performance. Thus, with the device shown in FIG. 1 introduced into the patient's esophagus and stomach, pacing pulses having different patterns, including pulse rates, amplitudes, durations, etc., can be delivered to electrodes 16 and 26, respectively, accompanied by echocardiographic monitoring. This procedure will allow the physician to determine the optimum settings for a pacemaker, which can then be permanently implanted according to conventional techniques, and will facilitate preplanning of the type of pacemaker to be employed.

A system of the type shown in FIG. 2 can thus be employed for testing atrial pacing, ventricular pacing, or atrial-ventricular pacing. It can be used to measure time intervals between a pacing pulse and a particular heart response, such as the AV delay or the VA delay. It can be employed to produce external stimuli which cause arrhythmias or to determine the efficacy of any drug treatment being performed on the patient. In addition, a system according to the invention can be employed to determine the programming parameters for a pacemaker prior to implantation.

Because of the manner in which a device according to the invention is introduced into a patient, all of the procedures described herein can be performed on an outpatient basis.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. Device for effecting ventricular cardiac pacing, comprising:
   a plurality of ventricular pacing electrodes;
   a carrier supporting said ventricular pacing electrodes in a manner to permit said ventricular pacing electrodes to be inserted into the stomach of a patient via the patient's esophagus; and
   carrier displacing means coupled to said ventricular pacing electrodes and operable for pressing said ventricular pacing electrodes against the wall of the stomach.

2. The device of claim 1 wherein said carrier is a flexible tube which can be advanced along the patient's esophagus.

3. The device of claim 2 wherein said carrier displacing means comprise a balloon mounted on said carrier.

4. The device of claim 3 wherein said carrier is a catheter of electrical insulating material.

5. The device of claim 4 wherein said catheter has a distal end portion carrying said electrodes and said balloon is composed of two subportions having respectively different compliances, one of the subportions having a higher compliance and contacting said distal end portion of said catheter.

6. The device of claim 5 further comprising a plurality of conductors extending through said carrier and each connected to a respective one of said ventricular pacing electrodes.

7. The device of claim 1 further comprising atrial pacing means mounted on said carrier for applying heart pacing signals to a heart atrium via the patient's esophagus.

8. The device of claim 7 wherein said atrial pacing means comprise a plurality of atrial pacing electrodes for producing heart pacing signals and an inflatable member for pressing said atrial pacing electrodes against the patient's esophagus.

9. The device of claim 1 wherein said carrier has a distal end portion which carries said ventricular pacing electrodes and said carrier has a length sufficient to locate said distal end portion in the stomach of a patient when said carrier has been introduced through the esophagus of the patient.

10. A method for effecting ventricular cardiac pacing comprising:
   inserting a plurality of electrodes into a patient's stomach via the patient's esophagus;
   pressing at least two of the electrodes against a portion of the wall of the stomach which is adjacent a heart ventricle; and
   conducting electrical pulse signals between the heart ventricle and external signal processing equipment via the at least two electrodes.

11. The method of claim 10 wherein said step of conducting electrical pulse signals comprises delivering electrical impulses to the at least two electrodes for transfer to the heart ventricle as pacing pulses.

12. The method of claim 11 wherein: the electrodes are carried on a balloon; and said step of inserting comprises mounting the balloon in a tubular carrier and passing the tubular carrier through the patient's esophagus.

13. The method of claim 12 wherein said step of pressing is carried out by inflating the balloon after said step of inserting.

14. A system for performing electrophysiological testing, comprising:
   the device defined in claim 8;
   pulse generator and receiver means connected to at least two of said ventricular pacing electrodes and at least two of said atrial pacing electrodes for delivering pacing pulses to selected electrodes and for receiving electrical signals induced in selected electrodes;
   control means connected to said pulse generator and receiver means for controlling generation of the pacing pulses; and
   monitoring means connected to said pulse generator and receiver means for displaying data representative of parameters of electrical signals induced in the at least one of the electrodes.

15. A method for performing electrophysiological testing, using the system of claim 14, comprising:

inserting said device into a patient's esophagus and stomach so that said at least two ventricular pacing electrodes are pressed against the wall of the stomach at a location adjacent a heart ventricle and said at least two atrial pacing electrodes are pressed against the esophagus at a location adjacent a heart atrium;

delivering pacing pulses to selected electrodes via said pulse generator and receiver means;

varying at least one parameter of the pacing pulses; and monitoring signals delivered from the patient's heart to selected electrodes.

* * * * *